(12) United States Patent
Lim et al.

(10) Patent No.: US 10,758,735 B2
(45) Date of Patent: Sep. 1, 2020

(54) IMPLANTABLE MEDICAL DEVICE HAVING AN ELECTRODE AND ANTENNA PROVIDED WITH A CERAMIC HEADER

(71) Applicant: PACESETTER, INC., Sylmar, CA (US)

(72) Inventors: Wisit Lim, Santa Clarita, CA (US); Perry Li, Arcadia, CA (US)

(73) Assignee: PACESETTER, INC., Sylmar, CA (US)

( * ) Notice: Subject to any disclaimer, the term of this patent is extended or adjusted under 35 U.S.C. 154(b) by 137 days.

(21) Appl. No.: 15/886,709

(22) Filed: Feb. 1, 2018

(65) Prior Publication Data

US 2019/0232066 A1    Aug. 1, 2019

(51) Int. Cl.
| | | |
|---|---|---|
| *A61N 1/375* | (2006.01) | |
| *A61N 1/37* | (2006.01) | |
| *A61N 1/05* | (2006.01) | |
| *A61B 5/042* | (2006.01) | |
| *A61B 5/00* | (2006.01) | |
| *A61N 1/372* | (2006.01) | |

(52) U.S. Cl.
CPC ............ *A61N 1/3756* (2013.01); *A61B 5/042* (2013.01); *A61B 5/686* (2013.01); *A61N 1/37* (2013.01); *A61N 1/3754* (2013.01); *A61N 1/37512* (2017.08); *A61B 5/0031* (2013.01); *A61B 2560/0468* (2013.01); *A61N 1/37229* (2013.01); *A61N 1/37252* (2013.01)

(58) Field of Classification Search
CPC .......... A61N 1/05; A61N 1/372; A61N 1/375; A61N 1/39; A61N 1/362; A61B 7/04; A61B 5/11; A61B 5/0205; A61B 5/00
USPC ........................................................ 607/116
See application file for complete search history.

(56) References Cited

U.S. PATENT DOCUMENTS

| | | |
|---|---|---|
| 8,135,456 B2 | 3/2012 | Haluska |
| 8,391,980 B2 | 3/2013 | Bomzin et al. |
| 8,831,747 B1 | 9/2014 | Min et al. |
| 9,044,610 B2 | 6/2015 | Rosenberg et al. |
| 9,216,285 B1 | 12/2015 | Boling et al. |
| 9,232,485 B2 | 1/2016 | Wu et al. |
| 9,333,351 B2 | 5/2016 | Arnold et al. |
| 9,387,332 B2 | 7/2016 | Zhao et al. |
| 10,130,820 B2 * | 11/2018 | Bogban ................ A61B 5/0008 |

(Continued)

*Primary Examiner* — Jon Eric C Morales
(74) *Attorney, Agent, or Firm* — The Small Patent Law Group LLC; Dean D. Small

(57) ABSTRACT

Methods and devices are provided for implantable medical devices. The device comprises a device housing that has an electronics module, an electrode, an antenna, and a header that has a main body. The main body is formed of a ceramic material that includes side walls, a distal end and a proximal mounting end. The main body has an electrode retention region and an antenna retention platform. The antenna extends along the antenna retention platform. The electrode is provided at the electrode retention region. The mounting end includes electrode and antenna connectors. The main body includes a first plated trace formed through the ceramic material to be electrically coupled to the electronics module in the device housing. Between the antenna and the antenna connector, the main body includes a second plated trace formed through the ceramic material between the electrode and the electrode connector.

19 Claims, 14 Drawing Sheets

(56) References Cited

U.S. PATENT DOCUMENTS

| | | | |
|---|---|---|---|
| 2007/0288066 A1* | 12/2007 | Christman | A61N 1/37229 607/60 |
| 2014/0135882 A1* | 5/2014 | Prasannakumar | A61N 1/05 607/116 |
| 2017/0281957 A1* | 10/2017 | Howard | A61N 1/3754 |

* cited by examiner

IMPLANTABLE MEDICAL DEVICE HAVING AN ELECTRODE AND ANTENNA PROVIDED WITH A CERAMIC HEADER

BACKGROUND

Embodiments of the present disclosure generally relate to implantable medical devices and methods, and more particularly to implantable medical devices having an electrode and antenna provided in a ceramic header.

Various types of implantable devices are utilized today for monitoring physiologic activity and potentially delivering therapy. Some types of implantable devices are "leadless" and instead include electrodes directly on the housing to sense and deliver therapy. One example of an implantable device, that does not provide therapy, is an Implantable Cardiac Monitor (IMD), which is very small in size as compared to other implantable medical devices such as pacemakers, implantable cardioverter defibrillators, cardiac rhythm management devices and the like. The IMD includes a header that holds an antenna for wireless communications (e.g., an RF or Bluetooth Low Energy antenna). The IMD header also houses a sensing electrode to monitor physiologic activity of the patient. The header may be formed by an epoxy cast in-place on an end of a case or housing of the IMD. Optionally, the header may be pre-molded using a thermoplastic polyurethane composition, such as a Tecothane® composition, and then the pre-molded header is attached to the IMD housing.

However, an opportunity remains to improve upon conventional IMD designs. For example, the small size of the header presents difficulty in attaching the header to the IMD housing. Also, difficulties exist in managing a reliable adhesion of the header to the IMD housing.

A need remains for an implantable medical device that affords a reliable and simply manner of attachment between the header and the device housing, where the header includes an antenna and one or more electrodes.

SUMMARY

In accordance with embodiments herein, an implantable medical device is provided. The device comprises a device housing that electronics module, an electrode, an antenna, and a header that has a main body. The main body is formed of a ceramic material that includes side walls, a distal end and a proximal mounting end. The main body has an electrode retention region and an antenna retention platform. The antenna extends along the antenna retention platform. The electrode is provided at the electrode retention region. The mounting end includes electrode and antenna connectors. The main body includes a first plated trace formed through the ceramic material to be electrically coupled to the electronics module in the device housing. Between the antenna and the antenna connector, the main body includes a second plated trace formed through the ceramic material between the electrode and the electrode connector.

Optionally, the main body may represent a solid body formed of a generally monolithic homogeneous ceramic material that may include the first and second plated traces formed therein. The solid body of the ceramic material may have an exterior surface formed with projecting and recessed features that may define the electrode retention region and the antenna retention platform. A shell may be mounted over the main body. The shell may have openings there through to expose the electrode and the antenna through the one of the side walls and the distal end, respectively, of the main body. The shell may be bonded to the device housing. The shell may include first and second shell case portions that may include notched out portions that combine to form an opening through which the antenna retention platform projects.

Optionally, the device housing may include elongated opposed first and second cases that may include header shell segments. The header shell segments may mate with one another to overlap the side walls of the main body of the header. At least one of the header shell segments may have an opening there through to expose the electrode from the corresponding side of the header. The shell and the device housing may be formed of a common conductive material. The electrode retention recess and antenna retention platform may electrically separate the electrode and antenna from the shell and device housing. The shell may comprise a multipart ring frame mounted on the main body and a header shell segment formed with the device housing.

Optionally, the ring frame may include an electrode frame surrounding the electrode retention region and an antenna frame surrounding the antenna retention platform. The electrode and antenna frames may be bonded to the header shell segment. The device housing may include first and second case portions that may include first and second header shell segments, respectively. The ring frame may mate with and may be bonded to the first and second header shell segments. A feed-through assembly may be joined between the device housing and the header. The feed-through assembly may include conductors that have distal ends connected to the electronics module and have proximal ends projecting from the feed-through assembly and joined to the antenna connector and electrode connector to electrically couple the electrode and antenna to the electronics module in the device housing.

Optionally, the header may be directly mounted to a proximal end of the device housing in a feedthrough-less configuration. The antenna may be embedded within the antenna retention platform and may extend along an interior cavity within the platform proximate to the distal end. The device may further comprise a battery that may have a battery shell formed of a material to be exposed to and biocompatible with a physiologic environment of the implant area. The battery may be connected to the electronics module and not enclosed within the device housing.

In accordance with embodiments herein a header for an implantable medical device is provided. The device comprises an electrode, an antenna, and a main body formed of a ceramic material that includes side walls, a distal end and a proximal mounting end. The main body has an electrode retention region and an antenna retention platform. The antenna extends along the antenna retention platform. The electrode is provided at the electrode retention region. The mounting end includes electrode and antenna connectors that are configured to be electrically coupled to an electronics module in a device housing. The main body includes a first plated trace formed through the ceramic material between the antenna and the antenna connector. The main body includes a second plated trace formed through the ceramic material between the electrode and the electrode connector.

Optionally, the main body may represent a solid body formed of a generally homogeneous ceramic material that may include the first and second plated traces formed therein. The solid body of the ceramic material has an exterior surface formed with projecting and recessed features to define an electrode retention region and an antenna retention platform.

In accordance with embodiments herein, a method to provide an implantable medical device is provided. The method mounts an electronics module in a device housing. The method provides a header by forming a main body of a ceramic material that includes side walls, a distal end and a proximal mounting end. The main body has an electrode retention region and an antenna retention platform. The header locates an antenna to extend along the antenna retention platform, locates an electrode at the electrode retention region and inserts electrode and antenna connectors at the mounting end. The main body includes a first plated trace formed through the ceramic material between the antenna and the antenna connector. The main body includes a second plated trace formed through the ceramic material between the electrode and the electrode connector. The method attaches the header to the device housing with the antenna and electrode connectors electrically coupled to the electronics module in the device housing.

Optionally, the forming operation may include forming the main body as a solid body of a generally monolithic homogeneous ceramic material that includes the first and second plated traces formed therein and forming an exterior surface of the solid body with projecting and recessed features to define the electrode retention region and the antenna retention platform. The method may mount a shell over the main body. The method may provide openings through the shell to expose the electrode and the antenna through the one of the side walls and the distal end, respectively, of the main body. The method may bond the shell to the device housing. The attaching operation may include directly mounting the header to a proximal end of the electronics module in a feedthrough-less configuration. The method may enclose the header and electronics module in the device housing.

DETAILED DESCRIPTION

Figure 1A:
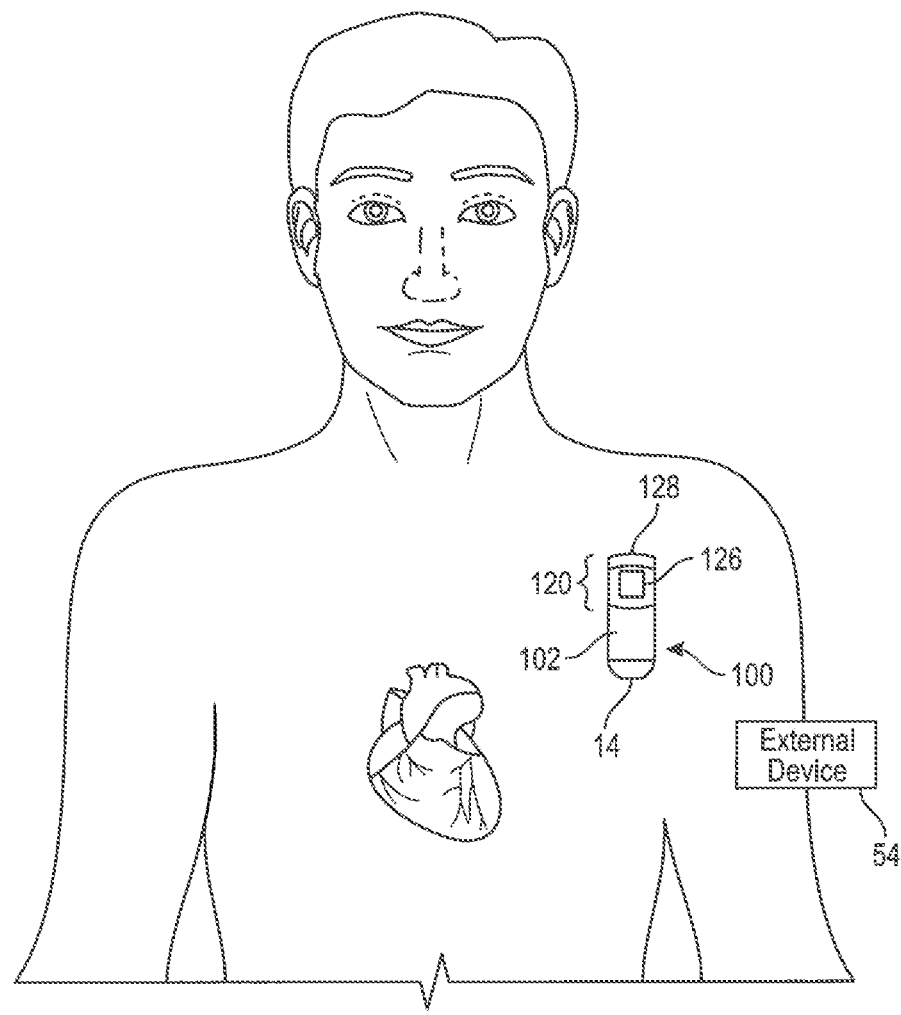
FIG. 1A illustrates an implantable medical device (IMD) intended for subcutaneous implantation at a site near the heart in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The terms "non-feedthrough configuration" and "feedthrough-less configuration" are used throughout to refer to embodiments in which the header is physically and directly mounted to or within a proximal end of the device housing without any intervening feedthrough assembly. By way of example, the embodiments illustrated in FIGS. 7-11 represent nonlimiting examples of non-feedthrough configurations.

The term "integrated" refers to a manner of interconnection between an electrode, antenna and ceramic header body, wherein the ceramic header body is molded or machined to include predetermined projecting and recessed features that are sized and dimensioned to conform to and receive corresponding features of the electrode and antenna.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, leadless pacemaker, cardioverter, cardiac rhythm management device, defibrillator, neurostimulator, and the like. For example, the IMD may include one or more structural and/or functional aspects of the device(s) described in U.S. Pat. No. 9,333,351 ("Neurostimulation Method And System To Treat Apnea") and U.S. Pat. No. 9,044,610 ("System And Methods For Providing A Distributed Virtual Stimulation Cathode For Use With An Implantable Neurostimulation System"), which are hereby incorporated by reference. Additionally or alternatively, the IMD may include one or more structural and/or functional aspects of the device(s) described in U.S. Pat. No. 9,216,285 ("Leadless Implantable Medical Device Having Removable And Fixed Components") and U.S. Pat. No. 8,831,747 ("Leadless Neurostimulation Device And Method Including The Same"), which are hereby incorporated by reference. Additionally or alternatively, the IMD may include one or more structural and/or functional aspects of the device(s) described in U.S. Pat. No. 8,391,980 ("Method And System For Identifying A Potential Lead Failure In An Implantable Medical Device") and U.S. Pat. No. 9,232,485 ("System And Method For Selectively Communicating With An Implantable Medical Device"), which are hereby incorporated by reference.

FIG. 1A illustrates an implantable medical device (IMD) 100 intended for subcutaneous implantation at a site near the heart. The IMD 100 may provide comprehensive safe diagnostic data reports including a summary of heart rate, in order to assist physicians in diagnosis and treatment of patient conditions. By way of example, reports may include episodal diagnostics for auto trigger events, episode duration, episode count, episode date/time stamp and heart rate histograms. The IMD 100 may be configured to be relatively small (e.g., between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

The IMD 100 provides a data storage option that is simple to configure to enable physicians to prioritize data based on individual patient conditions, to capture significant events and reduce risk that unexpected events are missed. The IMD 100 may be programmable pre- and post-trigger event storage. For example, the IMD 100 may be automatically activated to store 10-60 seconds of activity data prior to an event of interest and/or to store 10-60 seconds of post event activity. Optionally, the IMD 100 may afford patient triggered activation in which pre-event activity data is stored, as well as post event activity data (e.g., pre-event storage of 1-105 minutes and post-event storage of 30-60 seconds). Optionally, the IMD 100 may afford manual (patient triggered) or automatic activation for EGM storage. Optionally, the IMD 100 may afford additional programming options (e.g., asystole duration, bradycardia rate, tachycardia rate, tachycardia cycle count). The amount of EGM storage may vary based upon the size of the memory.

The IMD 100 includes a housing 102 that is joined to a header 120. At least one electrode 126 and an antenna 128 are provided in the header 120 as explained hereafter in accordance with embodiments herein. In accordance with embodiments herein, a header configuration is provided in which the antenna 128 and electrode 126 are integrated into a ceramic body of the header 120 to provide a high degree of reliability during manufacturing. In addition, embodiments herein avoid the use of epoxy precast or Tecothane® compositions, within the header, and instead utilize ceramic to enclose the antenna 128, thereby allowing the antenna to be smaller and formed with a simpler shape as compared to current antenna designs in epoxy or Tecothane®. The ceramic main body of the header 120 is hermetically enclosed in a shell (e.g., a titanium shell) which reinforces the ceramic body.

The housing 102 includes one or more electrodes 14 that are provided on the housing 102 distal from the header 120. The electrode(s) 14 may be located in various locations on the housing 102. For example, when separate housing portions are provide for the electronics module and the battery, one or more electrodes may be located on the battery (e.g., the battery housing). Numerous configurations of electrode arrangements are possible.

The housing 102 includes various other components such as sensing electronics for receiving signals from the electrodes, a microprocessor for processing the signals in accordance with algorithms (e.g., an AF detection algorithm), a memory for temporary storage of electrograms, a device memory for long-term storage of electrograms upon certain triggering events, such as AF detection, sensors for detecting patient activity and a battery for powering components.

The IMD device 100 senses far field, subcutaneous electrograms, processes the electrograms to detect arrhythmias and automatically records the electrograms in memory for subsequent transmission through the antenna 128 to an external device 54. Electrogram processing and arrhythmia detection is provided for, at least in part, by algorithms embodied in the microprocessor. In one configuration, the monitoring device is operative to detect atrial fibrillation.

Figure 1B:
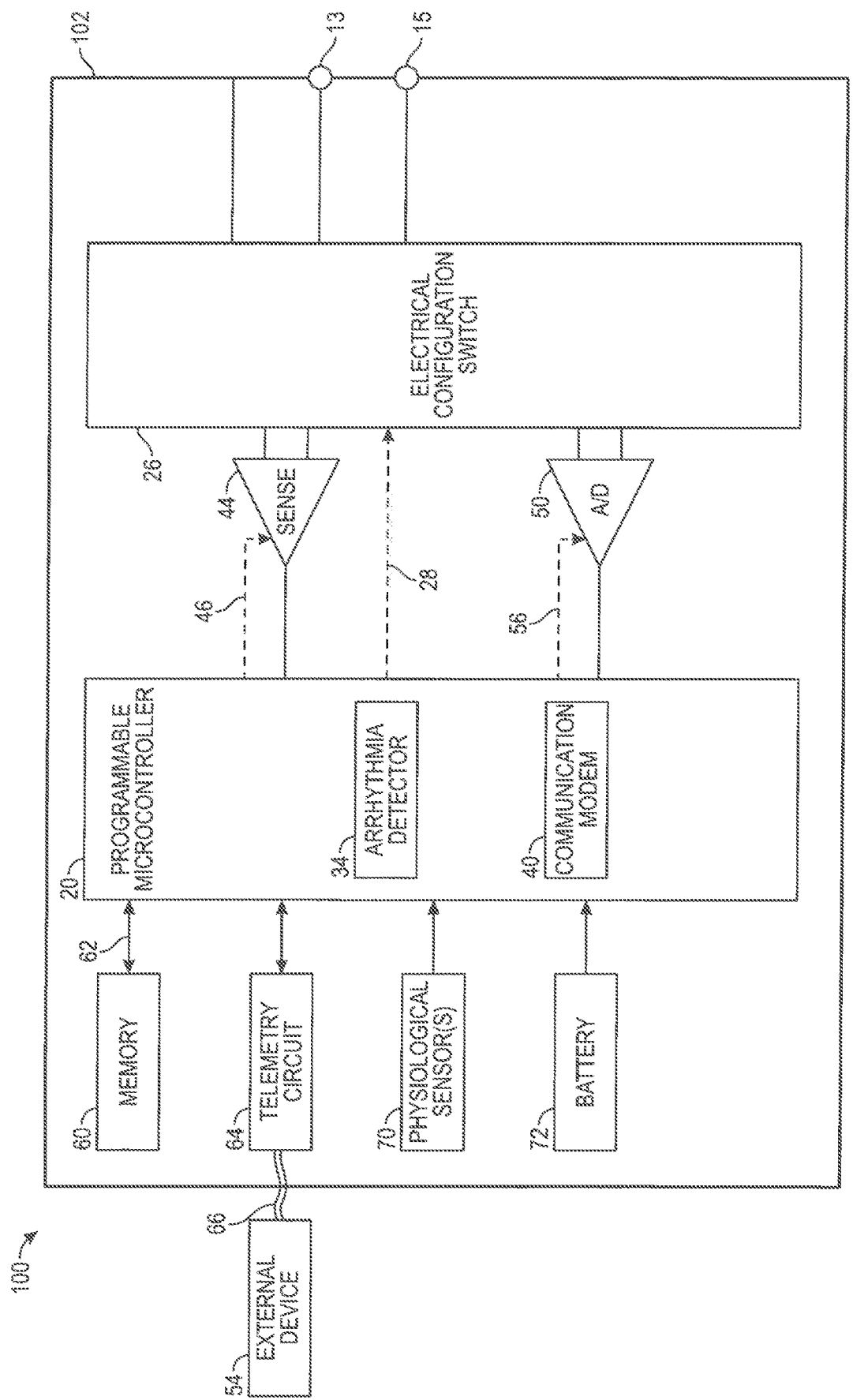
FIG. 1B shows a block diagram of an exemplary IMD that is configured to be implanted into the patient in accordance with embodiments herein.

FIG. 1B shows a block diagram of an exemplary IMD 100 (such as device 10) that is configured to be implanted into the patient. Optionally, the IMD 100 may be provided as an external device that is worn, held or otherwise located proximate to the patient during operation. The IMD 100 may be implemented to monitor ventricular activity alone, or both ventricular and atrial activity through sensing circuitry. The IMD 100 has a housing 102 to hold the electronic/computing components. The housing 102 (which is often referred to as the "can", "case", "encasing", or "case electrode") may be programmable to act as an electrode for certain sensing modes. The housing 102 further includes a connector (not shown) with at least one terminal 12 and preferably a second terminal 14. The terminals 13, 15 may be coupled to sensing electrodes that are provided upon or immediately adjacent the housing 102. Optionally, more than two terminals 13, 15 may be provided in order to support more than two sensing electrodes to support a true bipolar sensing scheme using the housing as a reference electrode. Additionally or alternatively, the terminals 13, 15 may be connected to one or more leads having one or more electrodes provided thereon, where the electrodes are located in various locations about the heart. The type and location of each electrode may vary.

In at least some embodiments, the IMD 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor—tissue interface. The IMD 100 may be configured to be activated by the patient or automatically activated, in connection with recording subcutaneous ECG signals.

The IMD 100 includes a programmable microcontroller 20 that controls various operations of the IMD 100, including cardiac monitoring. Microcontroller 20 includes a microprocessor (or equivalent control circuitry), RAM and/or ROM memory, logic and timing circuitry, state machine circuitry, and I/O circuitry. The microcontroller 20 also performs the operations described herein in connection with collecting cardiac activity data and analyzing the cardiac activity data to identify episodes.

A switch 26 is optionally provided to allow selection of different electrode configurations under the control of the microcontroller 20. The electrode configuration switch 26 may include multiple switches for connecting the desired electrodes to the appropriate I/O circuits, thereby facilitating electrode programmability. For example, the switch 26 may be utilized to select between electrodes 126 provided on opposite sides of the header 120, such as based upon the orientation of the IMD 100 relative to a physiologic area of interest. The switch 26 is controlled by a control signal 28 from the microcontroller 20. Optionally, the switch 26 may be omitted and the I/O circuits directly connected to the housing electrode and a second electrode. Microcontroller 20 includes an arrhythmia detector 34. The arrhythmia detector 34 is configured to analyze cardiac activity data to identify potential AF episodes as well as other arrhythmias (e.g., Tachycardias, Bradycardias, Asystole, etc.). By way of example, the arrhythmia detector 34 may implement an AF detection algorithm as described in U.S. Pat. 8,135,456, the complete subject matter of which is incorporated herein by reference. In accordance with at least some embodiments, when a potential AF episode is detected, the detector is utilized to determine whether the episode is in fact an AF episode or instead another episode. Although not shown, the microcontroller 20 may further include other dedicated circuitry and/or firmware/software components that assist in monitoring various conditions of the patient's heart and managing pacing therapies.

The IMD 100 is further equipped with a communication modem (modulator/demodulator) 40 to enable wireless communication. In one implementation, the communication modem 40 uses high frequency modulation, for example using RF, Blue Tooth, Blue Tooth Low Energy and other telemetry protocols. The signals are transmitted in a high frequency range and will travel through the body tissue in fluids without stimulating the heart or being felt by the patient. The communication modem 40 may be implemented in hardware as part of the microcontroller 20, or as software/firmware instructions programmed into and executed by the microcontroller 20. Alternatively, the modem 40 may reside separately from the microcontroller as a standalone component. The modem 40 facilitates data retrieval from a remote monitoring network. The modem 40 enables timely and accurate data transfer directly from the patient to an electronic device utilized by a physician.

The IMD 100 includes sensing circuitry 44 selectively coupled to one or more electrodes that perform sensing operations, through the switch 26 to detect cardiac activity data indicative of cardiac activity. The sensing circuitry 44 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. In one embodiment, switch 26 may be used to determine the sensing polarity of the cardiac signal by selectively closing the appropriate switches.

The output of the sensing circuitry 44 is connected to the microcontroller 20 which, in turn, determines when to store the cardiac activity data (digitized by the A/D data acquisition system 50) in the memory 60. For example, the microcontroller 20 may only store the cardiac activity data (from the A/D data acquisition system 50) in the memory 60 when a potential AF episode is detected. The sensing circuitry 44 receives a control signal 46 from the microcontroller 20 for purposes of controlling the gain, threshold, polarization charge removal circuitry (not shown), and the timing of any blocking circuitry (not shown) coupled to the inputs of the sensing circuitry.

In the example of FIG. 1B, a single sensing circuit 44 is illustrated. Optionally, the IMD 100 may include multiple sensing circuits, similar to sensing circuit 44, where each sensing circuit is coupled to two or more electrodes and controlled by the microcontroller 20 to sense electrical activity detected at the corresponding two or more electrodes. The sensing circuit 44 may operate in a unipolar sensing configuration (e.g., housing 102 to electrode) or in a bipolar sensing configuration (e.g., between electrodes referenced to the housing electrode). Optionally, the sensing circuit 44 may be removed entirely and the microcontroller 20 perform the operations described herein based upon the EGM signals from the A/D data acquisition system 50 directly coupled to the electrodes 12 and/or 14.

The IMD 100 further includes an analog-to-digital A/D data acquisition system (DAS) 50 coupled to one or more electrodes via the switch 26 to sample cardiac signals across any pair of desired electrodes. The data acquisition system 50 is configured to acquire cardiac electrogram (EGM) signals, convert the raw analog data into digital data, and store the digital data for later processing and/or telemetric transmission to an external device 54 (e.g., a programmer, local transceiver, or a diagnostic system analyzer). The data acquisition system 50 is controlled by a control signal 56 from the microcontroller 20. The EGM signals are utilized as the cardiac activity data that is analyzed for potential episodes.

By way of example, the external device 54 may represent a portable smartphone, tablet device, bedside monitor installed in a patient's home and the like. The external device 54 is utilized to communicate with the IMD 100 while the patient is at work, home, in bed or asleep. The external device 54 may be a programmer used in the clinic to interrogate the device, retrieve data and program detection criteria and other features. The external device 54 may be a device that can be coupled over a network (e.g., the Internet) to a remote monitoring service, medical network and the like. The external device 54 facilitates access by physicians to patient data as well as permitting the physician to review real-time ECG signals while being collected by the IMD 100.

The microcontroller 20 is coupled to a memory 60 by a suitable data/address bus 62. The programmable operating parameters used by the microcontroller 20 are stored in memory 60 and used to customize the operation of the IMD 100 to suit the needs of a particular patient. Such operating parameters define, for example, detection rate thresholds, sensitivity, automatic features, arrhythmia detection criteria, activity sensing or other physiological sensors, and electrode polarity, etc.

In addition, the memory 60 stores the cardiac activity data, as well as the markers and other data content associated with detection of episodes. The operating parameters of the IMD 100 may be non-invasively programmed into the memory 60 through a telemetry circuit 64 in telemetric communication via communication link 66 with the external device 54. The telemetry circuit 64 allows intracardiac electrograms and status information relating to the operation of the IMD 100 (as contained in the microcontroller 20 or memory 60) to be sent to the external device 54 through the established communication link 66. In accordance with embodiments herein, the telemetry circuit 64 conveys the cardiac activity data, markers and other information related to AF episodes, The IMD 100 may further include magnet detection circuitry (not shown), coupled to the microcontroller 20, to detect when a magnet is placed over the IMD. A magnet may be used by a clinician to perform various test functions of the IMD 100 102 and/or to signal the microcontroller 20 that the external device 54 is in place to receive or transmit data to the microcontroller 20 through the telemetry circuits 64.

The IMD 100 can further include one or more physiologic sensor 70. Such sensors are commonly referred to (in the pacemaker arts) as "rate-responsive" or "exercise" sensors. The physiological sensor 70 may further be used to detect changes in the physiological condition of the heart, or diurnal changes in activity (e.g., detecting sleep and wake states). Signals generated by the physiological sensors 70 are passed to the microcontroller 20 for analysis and optional storage in the memory 60 in connection with the cardiac activity data, markers, episode information and the like. While shown as being included within the IMD 100, the physiologic sensor(s) 70 may be external to the IMD 100, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 72 provides operating power to all of the components in the IMD 100. The battery 72 is capable of operating at low current drains for long periods of time. The battery 72 also desirably has a predictable discharge characteristic so that elective replacement time can be detected. As one example, the unit 102 employs lithium/silver vanadium oxide batteries. The battery 72 may afford various periods of longevity (e.g., three years or more of device monitoring). In alternate embodiments, the batter 72 could be rechargeable. See for example, U.S. Pat. No. 7,294,108, Cardiac event microrecorder and method for implanting same, which is hereby incorporated by reference.

Header Configurations

Figure 2A:
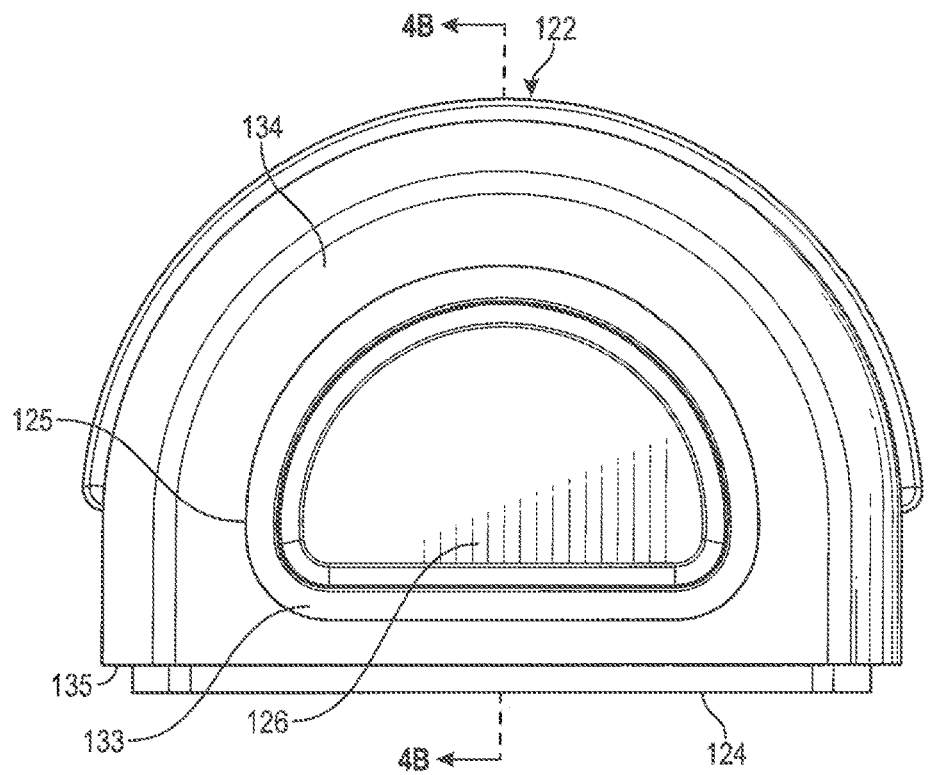
FIG. 2A illustrates a side perspective view of the header of FIG. 1A formed in accordance with embodiments herein.
Figure 2B:
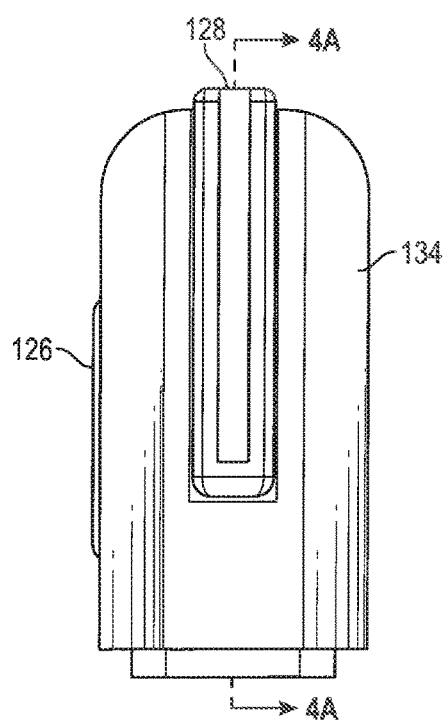
FIG. 2B illustrates an end perspective view of the header of FIG. 1A formed in accordance with embodiments herein.

FIGS. 2A and 2B illustrate side and end perspective views, respectively, of the header 120 of FIG. 1A formed in accordance with embodiments herein. The header 120 generally has a semi-circular side profile as viewed from the side (FIG. 2A), and a rectangular end profile as viewed from the end (FIG. 2B), although alternative profiles may be utilized. The header 120 includes a main body 122 and a shell 134. The main body 122 is formed with a mounting end 124 configured to be mounted to a feedthrough assembly that is mounted to the housing 102 of the IMD 100. Optionally, the mounting end 124 may be mounted directly to a proximal end of the housing 102 of the IMD 100. The main body 122 represents a solid (non-hollow) body formed of a generally monolithic homogeneous ceramic material that includes one or more plated traces formed therein (as described below in more detail). An exterior surface of the ceramic material, that defines the main body 122, is formed with certain projecting and recessed features to define, among other things, an electrode retention region and an antenna retention platform.

The shell 134 is mounted over the main body 122 and includes an opening there through to expose the electrode 126 through a sidewall of the shell 134. The shell 134 also includes an opening to expose the antenna 128 through the distal end of the header 120. The shell 134 includes a device case mounting edge 135 that is configured to directly abut against, and be bonded to, a mating end of the device housing 102. The shell 134 and the device housing 102 may be formed of a common conductive material or similar conductive materials that facilitate bonding to one another, such as through welding and other bonding techniques. As one non-limiting example, the shell 134 and the device housing 102 may be formed from titanium or another conductive, biocompatible material. By forming the shell 134 from titanium or another similar material, the shell 134 provides a protective cover over the ceramic material of the main body 122. Optionally, the shell 134 and/or the device housing 102 may be formed of a nonconductive biocompatible material that also exhibits desired protective properties.

As shown in FIG. 2A, the main body 122 receives and retains the electrode 126 at a position generally in a central area of the side of the header 120. By way of example, the electrode 126 is D-shaped or semi-circular, although other shapes may be utilized (e.g., circular, rectangular, triangular, oval, square, etc.). The electrode 126 is generally centered on the side of the header 120, although the electrode 126 may be positioned at different locations on the side. The electrode 126 is shown to cover approximately half of the surface area of the side of the header 120, although the electrode 126 may vary in size to encompass more or less total surface area on the side of the header 120. As one example, the electrode 126 may be formed with a surface area that is 40%-80%, and preferably 50%-80% of a total surface area of the side of the header 120. The surface area of the electrode 126 is determined in part based on sensing characteristics of interest.

In the present example, a single electrode 126 is illustrated on the first side of the header 120. Optionally, multiple electrodes 126 may be provided on the same side of the header 120. The multiple electrodes 126 may be formed electrically common with one another or electrically separate from one another. In the present example, the electrode 126 is shown on a first side of the header 120. Optionally, the electrode 126 may be moved to an opposite second side of the header 120. As a further option, first and second electrodes 126 may be provided on opposite sides of the header 120. When more than one electrode 126 is provided, a single electrode 126 (or a combination or all or a subset of the electrodes 126) may be actively utilized to sense physiologic signals. For example, an electrode on a first side may be activated, while an electrode on a second side may be in-active, such as based on the orientation of the IMD when implanted (e,g., activate the electrode facing the heart). Optionally, more than one electrode 126 may be provided on one side of the header 120.

Figure 3:
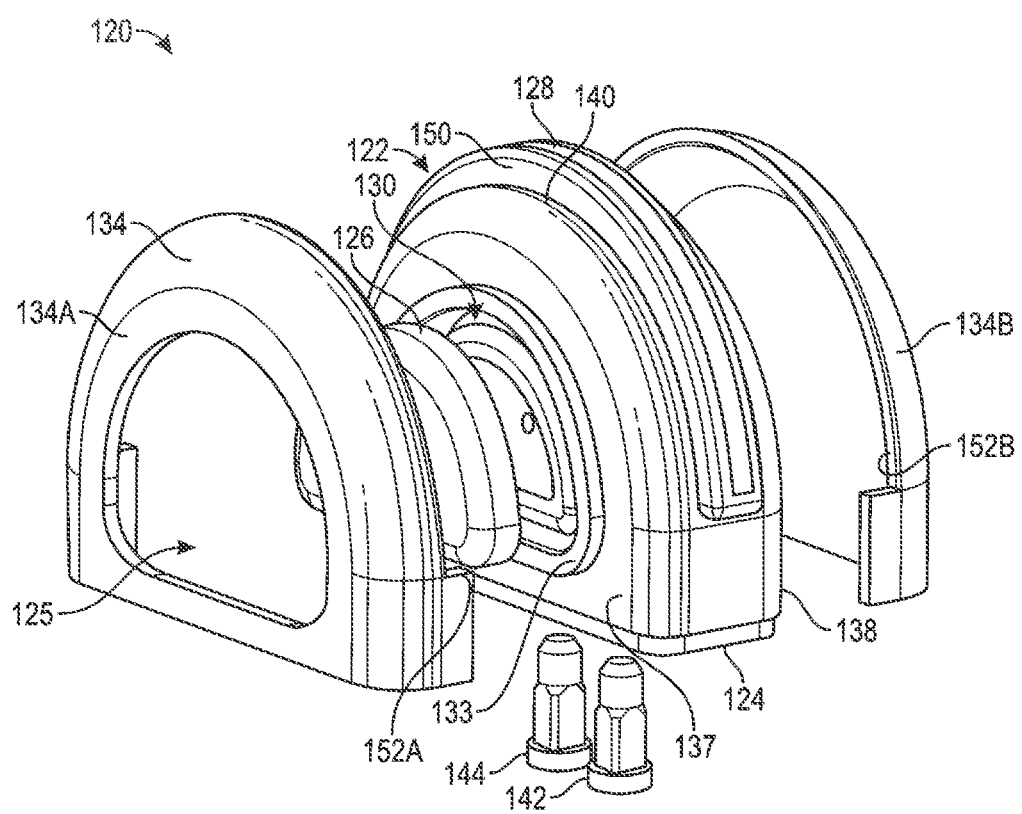
FIG. 3 illustrates an exploded view of the header in accordance with an embodiment herein.

FIG. 3 illustrates an exploded view of the header 120 in accordance with an embodiment herein. As shown in FIG. 3, the main body 122 is formed of a solid (non-hollow) ceramic material that includes a proximal mounting end 124, sidewalls 137, 138 and a curved distal end 140. The distal end 140 is located opposite to the proximal mounting end 124. The antenna 128 is integrated into and extends along the distal end 140, while the electrode 126 is provided on one of the sidewalls 137, 138. The mounting end 124 includes cavities configured to receive an electrode connector 142 and an antenna connector 144 that are configured to be electrically coupled to the electronics module within the device housing 102 of the IMD 100. In the example of FIG. 3, the electrode and antenna connectors 142, 144 represent receptacle connectors that are configured to receive conductive pins extending from a feedthrough assembly (as described below). Additionally or alternatively, the electrode and antenna connectors 142, 144 may be formed as pins that extend from the mounting end 124, with the pins configured to be received in receptacles in a feedthrough. Optionally, a feedthrough assembly may be removed entirely and the electrode and antenna connectors 142, 144 formed as conductive pins that are inserted directly into receptacles mounted within a proximal end of the device housing.

The solid body of the ceramic material forming the main body 122 has exterior surfaces formed with projecting and recessed features to define an electrode retention region 130 and an antenna retention platform 150. Details of the electrode retention region 130 and antenna retention platform 150 are discussed below in more detail in connection with FIGS. 4A and 4B.

The shell 134 includes shell case portions 134A and 134B to join with one another to enclose the main body 122. The shell case portions 134A, 134B include notched out portions 152A and 152B that form an opening 151 (FIG. 4B), through which the antenna retention platform 150 projects. The shell case portion 134A includes an opening 125 that is sized and shaped to expose the electrode 126 there through. The opening 126 closely fits over a rib 133 defining an outer perimeter of the electrode retention region 130.

Figure 4A:
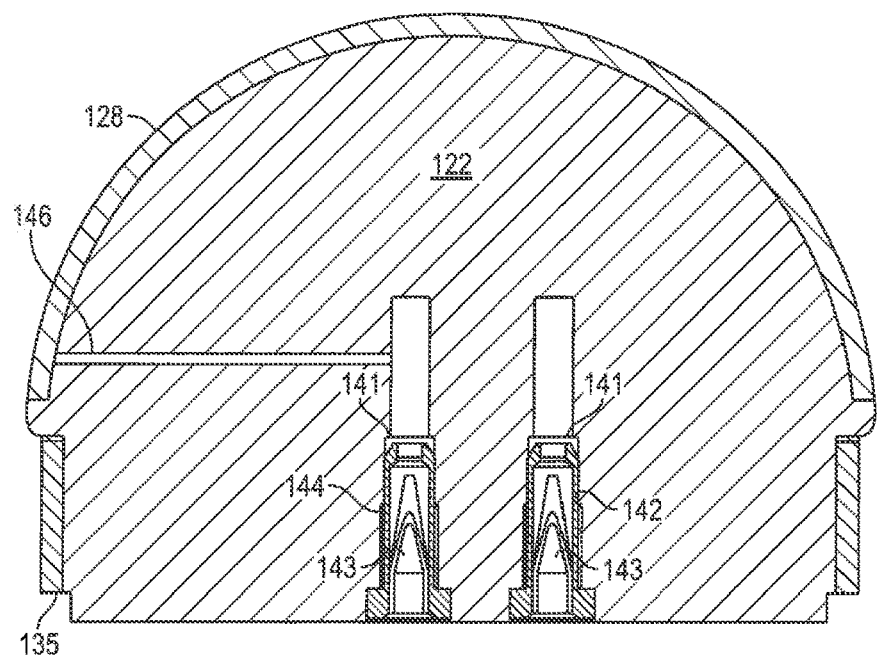
FIG. 4A illustrates a side sectional view taken along line 4A-4A in FIG. 2B in accordance with embodiments herein.
Figure 4B:
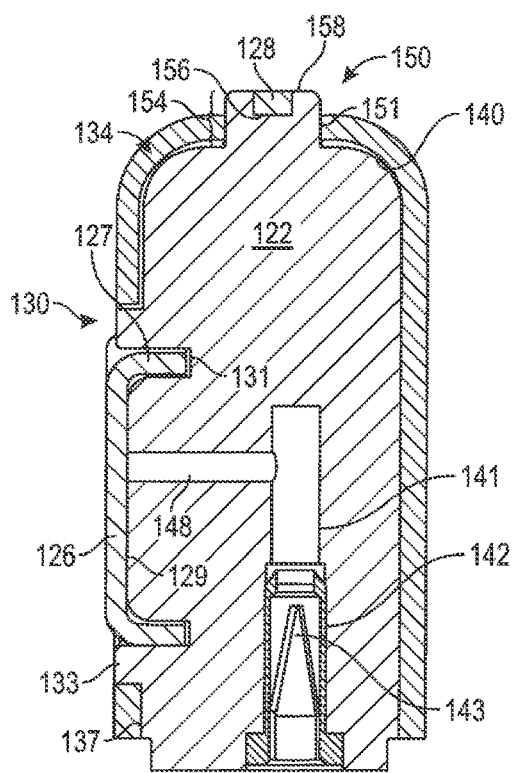
FIG. 4B illustrates an end sectional view taken along line 4B-4B in FIG. 2A in accordance with embodiments herein.

FIG. 4A illustrates a side sectional view taken along line 4A-4A in FIG. 2B in accordance with embodiments herein. FIG. 4B illustrates an end sectional view taken along line 4B-4B in FIG. 2A in accordance with embodiments herein. As shown in FIGS. 4A and 4B, the main body 122 is formed as a solid body of a generally monolithic homogeneous ceramic material. As shown in FIG. 4B, the sidewall 137 includes an electrode retention region 130 that holds an integrated electrode 126. By way of example, the electrode 126 may be gold braised onto the ceramic material of the main body 122 or bonded in another manner. The electrode 126 may be formed with a generally planar outer surface that extends generally parallel to the sidewall 137. Optionally, the electrode 126 may be bent to form a flange 127 that extends about a perimeter of the electrode 126. The electrode retention region 130 includes a central planar area 129 surrounded by a recess 131 that is shaped and dimensioned to receive the flange 127 around the perimeter of the electrode 126. The recess 131 and flanged 127 cooperate to facilitate positioning of the electrode 126 and to provide an interface to securely bond the electrode 126 to the main body 122. The electrode retention region 130 also includes a peripheral rib 133 that projects outward from the sidewall 137 and extends about an outer perimeter of the electrode 126. The opening 125 in the shell 134 is shaped and dimensioned to fit over the rib 133 with a close tolerance there between (as shown in FIG. 2A). The rib 133 forms a standoff to both center the shell 134 at a desired location relative to the main body 122, as well as to form a nonconductive barrier between the electrode 126 and the shell 134.

The antenna retention platform 150 projects outward through the opening 151 in the shell 134. The platform 150 extends a height 154 above the distal end 140 sufficient to locate the integrated antenna 128 at a desired spacing relative to the shell 134. The platform 150 includes a notch 156 extending about a perimeter of the platform 150. The notch 156 is surrounded by a dielectric border 158. The notch 156 is shaped and dimensioned to receive the antenna 128. The antenna 128 is recessed into the notch 156 in an integrated manner, with an outer surface of the antenna 128 substantially flush with an outer surface of the dielectric borders 158. The dielectric borders 158 separate the antenna 128 from adjacent portions of the shell 134 by a predetermined spacing to limit or entirely prevent antenna coupling between the antenna 128 and the adjacent portions of the shell 134. The main body 122, including the platform 150, is formed of ceramic which has a relatively high dielectric constant, as compared to other materials surrounding conventional antenna designs. Accordingly, embodiments herein enable the borders 158 to have a relatively thin thickness, thereby allowing a relatively small spacing between the antenna 128 and the proximal portions of the shell 134, as compared to conventional antenna designs.

It is desirable to avoid antenna coupling between the antenna 128 and the shell 134 as antenna coupling introduces additional capacitance into the transmission characteristics of the antenna 128, which would in turn require the antenna to include additional features to offset the added antenna coupling capacitance (e.g., adding a wide plated section and/or a zigzag pattern). By avoiding antenna coupling, embodiments herein reduce or prevent coupling capacitance between the antenna 128 and the shell 134, thereby avoiding the need for additional offsetting antenna features. The dielectric borders 158 extend substantially along a length of opposite sides of the antenna 128 to maintain a constant and even dielectric characteristic along opposite sides of the antenna 128.

By way of example, the antenna 128 may be formed as a monopole open loop antenna. The ceramic of the platform 150 exhibits a relatively high dielectric constant that allows the antenna 128 to be formed with a relatively small form factor. By way of example, surrounding at least three sides of the antenna 128 with ceramic material allows the antenna 128 to be formed in a singular arced curvature that bends along a relatively constant arc within a single plane. In the example of FIGS. 2A to 4B, the antenna 128 bends along a singular arc at an outer perimeter of the main body 122 (also referred to as a non-zig-zag, non-plated configuration). The antenna 128 avoids the need for added coupling capacitance offsetting features, such as a zigzag pattern or a wide plated section, as compared to conventional antenna designs.

By maintaining a high dielectric constant (e.g., relative to the dielectric of Tecothane® compositions by The Lubrizol Corporation) within the region between the antenna 128 and the adjacent portions of the shell 134, the platform 150 (and borders 158) may be formed with a relatively compact and small form factor, thereby allowing closer spacing between the antenna 128 and the shell 134 as compared to conventional antenna designs.

The shell 134 is welded to the main body 122 along the interfaces there between to form a hermetic seat. For example, the shell 134 and main body 122 may be welded to one another about the perimeter of the platform 150, and about the rib 133. Additionally or alternatively, the shell 134 may be welded to the main body 122 along the device case mounting edge 135. The device case mounting edge 135 of the shell 134 may be bonded, such as through welding, to a feedthrough assembly (when used) and/or directly to the device housing (when no feedthrough is used) to form a hermetic sealed header assembly. Additionally or alternatively, the mounting end 124 of the main body 122 may be bonded to the feedthrough assembly (when used) and/or directly to the device housing to form a hermetic seal there between. In accordance with embodiments herein, the shell 134 and main body 122 enable the header assembly to be hermetically sealed to the device housing through welding and other similar bonding techniques, without the need for a backfill process that is used in conventional designs. In accordance with embodiments herein, the shell 134 and main body 122 provide a simpler and more reliable manufacturing process for the header assembly.

FIG. 4A further illustrates the electrode connector 142 and antenna connector 144 mounted within receptacle cavities 141 formed in the main body 122 of the ceramic material. The electrode and antenna connectors 142, 144 may include springs 143 that frictionally engage pins inserted into the receptacles to form a secure conductive connection there between. With reference to FIG. 4A, a first plated trace 146 is formed through the ceramic material between the antenna 128 and the receptacle cavity 141 that holds the antenna connector 144. With reference to FIG. 4B, a second plated trace 148 is formed through the ceramic material between the electrode 126 and the receptacle cavity 141 that holds the electrode connector 142. The first and second plated traces 146, 148 and receptacle cavities 141 may be plated with a conductive material after being formed during the molding process for creating the main body 122. In the present example, the plated trace 146 is connected to an end of the antenna 128, although the plated trace 146 may extend along various alternative paths to attach to the antenna 128 at any desired point along the length of the antenna 128.

As shown in FIG. 4A, the main body 122 receives and retains the antenna 128 along a top outer edge of the distal end 140 that is located opposite to the feed through mounting end 124. Optionally, the antenna 128 may be located at various positions upon the exterior surface of the main body 122, provided that the antenna 128 is exposed through the shell 134 and provided with a dear line of sight external to the IMD 100 that is not encumbered by conductive material such as the shell 134.

Figure 5A:
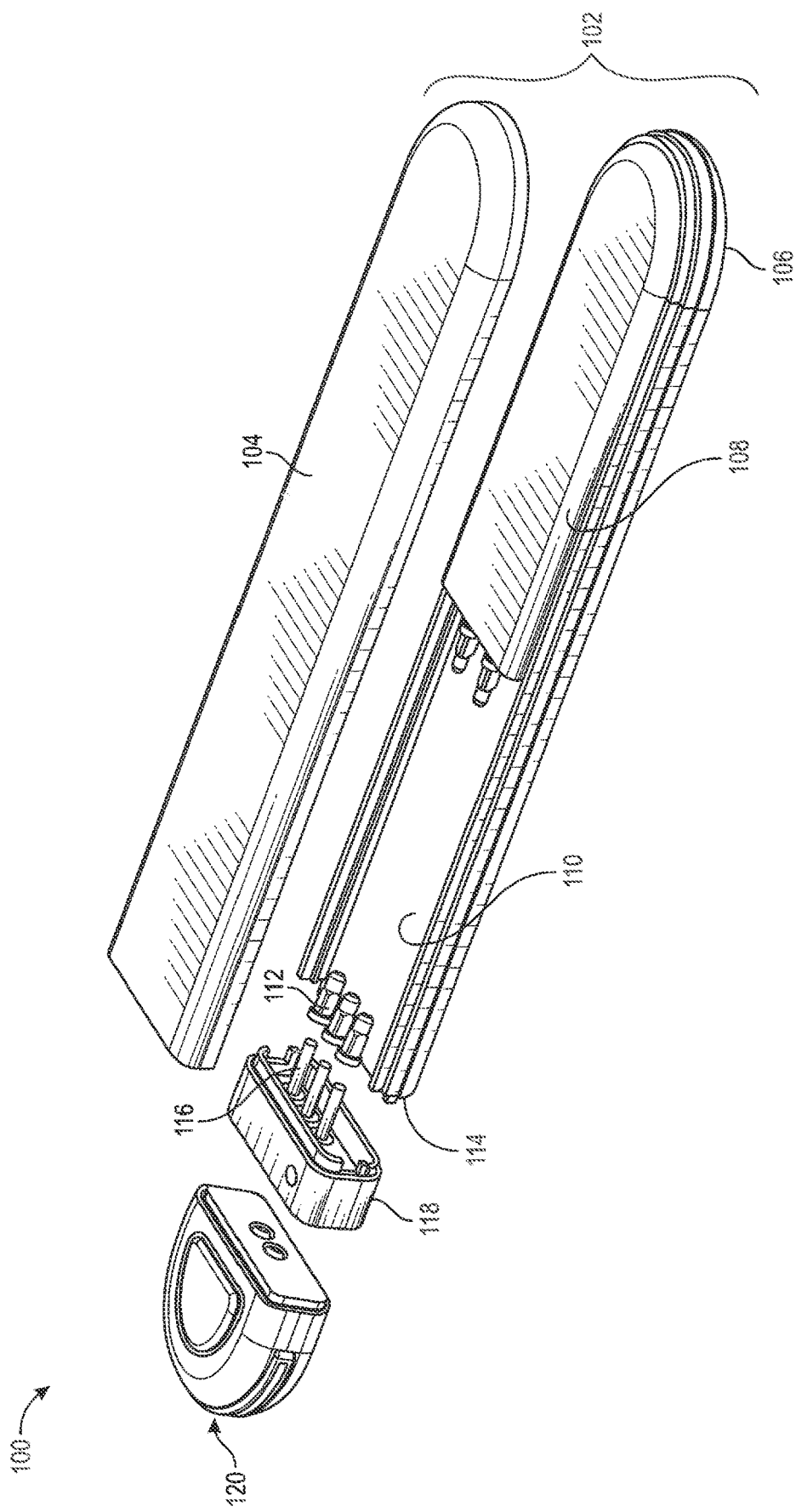
FIG. 5A illustrates a partially exploded perspective view of the IMD formed in accordance with embodiments herein.

FIG. 5A illustrates a partially exploded perspective view of the IMD 100 formed in accordance with embodiments herein. The device housing 102 is formed with top and bottom case portions 104, 106 that join with one another to enclose a battery 108 and an electronics module 110 (also referred to as a hybrid circuit). The electronics module 110 may include the components described above in connection with FIG. 1B, and/or as described in any of the patents or published applications incorporated herein by reference. The electronics module 110 includes a set of receptacles 112 provided proximate to a proximal end 114 of the device housing 102. The receptacles 112 are configured to receive and electrically couple with pins 116 extending from a bottom side of a feedthrough assembly 118. The pins 116 extend through the feedthrough assembly 118 to electrically couple with receptacle connectors within the header 120.

By way of example, during the assembly process, the battery 108 is attached to the electronics module 110 through the corresponding interface. The battery 108 and electronics nodule 110 are installed into the bottom case portion 106. Thereafter, the feedthrough assembly 118 is attached to the electronics module 110 by inserting the pins 116 into the receptacles 112 and firmly mounting the bottom side of the feedthrough assembly 118 onto the proximal end 114 of the bottom case portion 106. Next, the top case portion 104 is mounted to the bottom case portion 106 to enclose the battery 108 and electronics module 110. The header 120 is installed on the feedthrough assembly 118. Thereafter, the interfaces between the top and bottom case portions 104, 106, feedthrough assembly 118 and header 120 are seeded, such as through a welding process or other bonding technique to hermetically seal the interior components of the IMD 100.

Figure 5B:
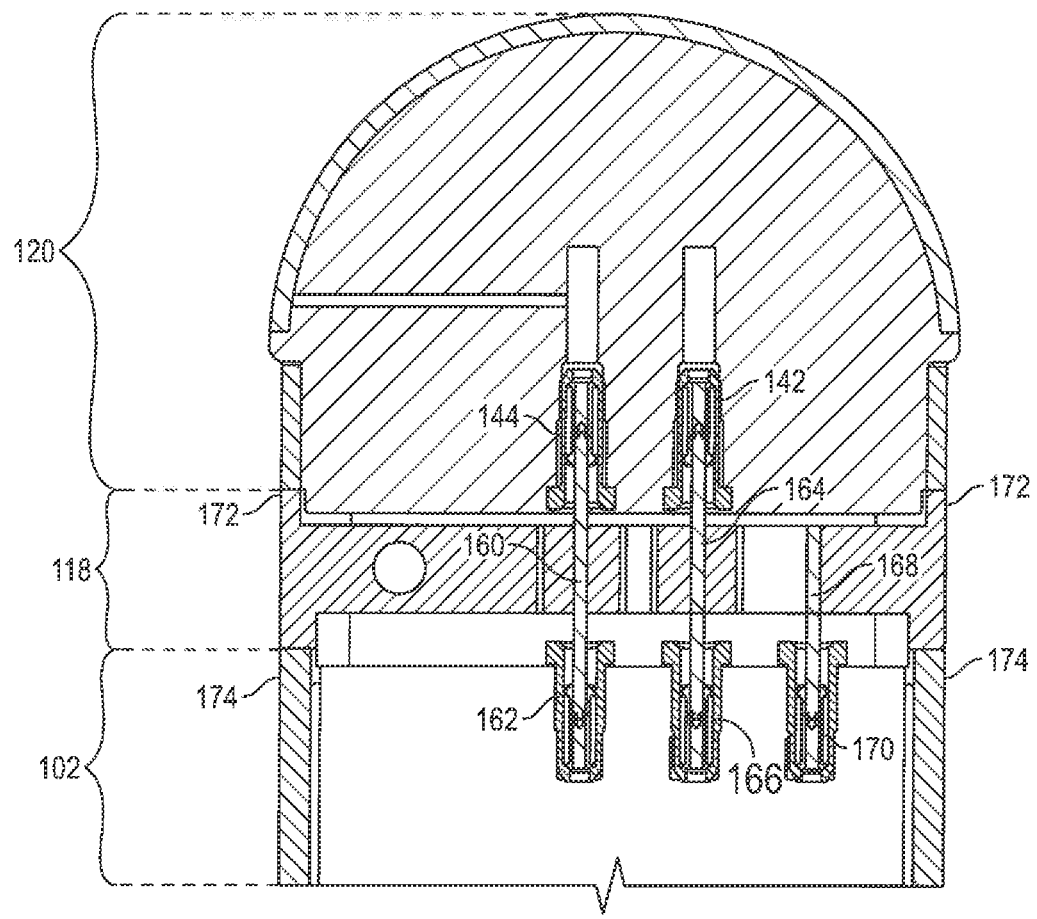
FIG. 5B illustrates a side sectional view of the proximal end of the IMD of FIG. 5A in accordance with embodiments herein.

FIG. 5B illustrates a side sectional view of the proximal end of the IMD 100 of FIG. 5A. As shown in FIG. 5B, the header 120 is seated onto the feedthrough assembly 118 which is mounted onto the proximal end of the device housing 102. An antenna pin 160 extends through the feedthrough assembly 118 and is electrically and physically engaged in receptacle antenna connectors 144 and 162 at the header 120 and device housing 102. An electrode pin 164 extends through the feedthrough assembly 118 and is electrically and physically engaged in receptacle electrode connectors 142 and 166. A grounding pin 168 is connected to a receptacle case connector 170 and the device housing 102. The antenna, electrode and ground pins 160, 164 and 168 engage springs within the corresponding connectors 144, 162, 142, 166 and 170. The header 120 is bonded to the feedthrough assembly 118 about header—feedthrough interface 172, while the feedthrough assembly 118 is bonded to the proximal end of the device housing 102 about feedthrough—housing interface 174.

Figure 6A:
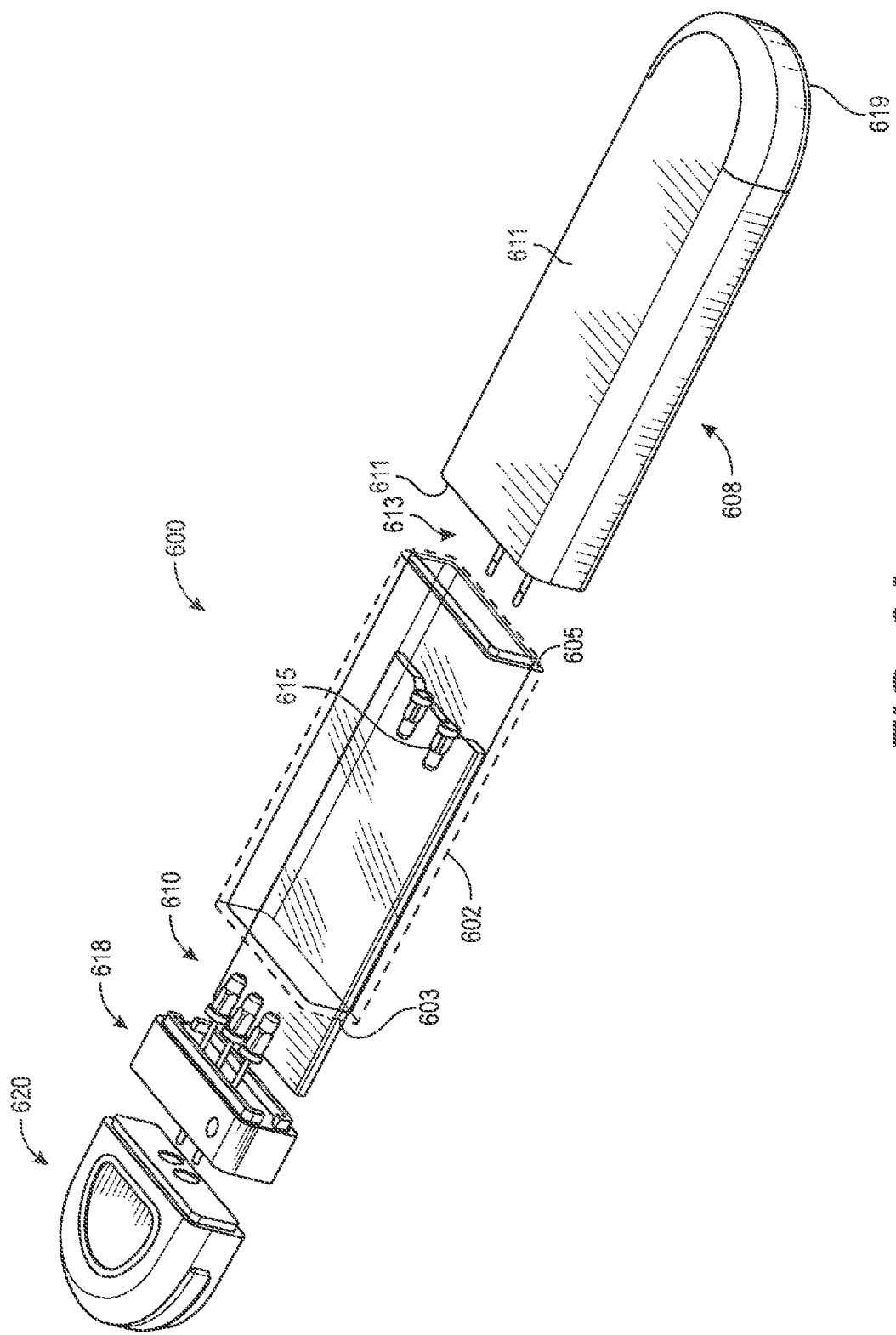
FIG. 6A illustrates an IMD formed in accordance with embodiments herein.

FIG. 6A illustrates an IMD 600 formed in accordance with an alternative embodiment. The IMD 600 includes a header 620, feedthrough 618 and electronics module 610 that are formed generally in the same manner as described above in connection with FIGS. 2A-5B. The embodiment of FIG. 6A differs from the embodiment of FIGS. 2A-B in that the battery is provided separate from the device housing. In FIG. 6A, a separate standalone battery 608 is provided that has a battery shell 611 formed of a material intended to be exposed to and biocompatible with the physiologic environment of the implant area. The battery 608 is not enclosed within the device housing. The battery 608 is provided with battery terminals 613 extending therefrom. A second electrode 619 is provided on the distal end of the battery 608.

The electronics module 610 is enclosed within a device housing 602 that includes a proximal end 603 and a distal end 605. The distal end 605 of the device housing 602 is abutted against and engages a proximal end 607 on the battery shell 611. The battery terminals 613 electrically engage battery receptacles 615 that are provided with the electronics module 610 on the hybrid circuit.

Figure 6B:
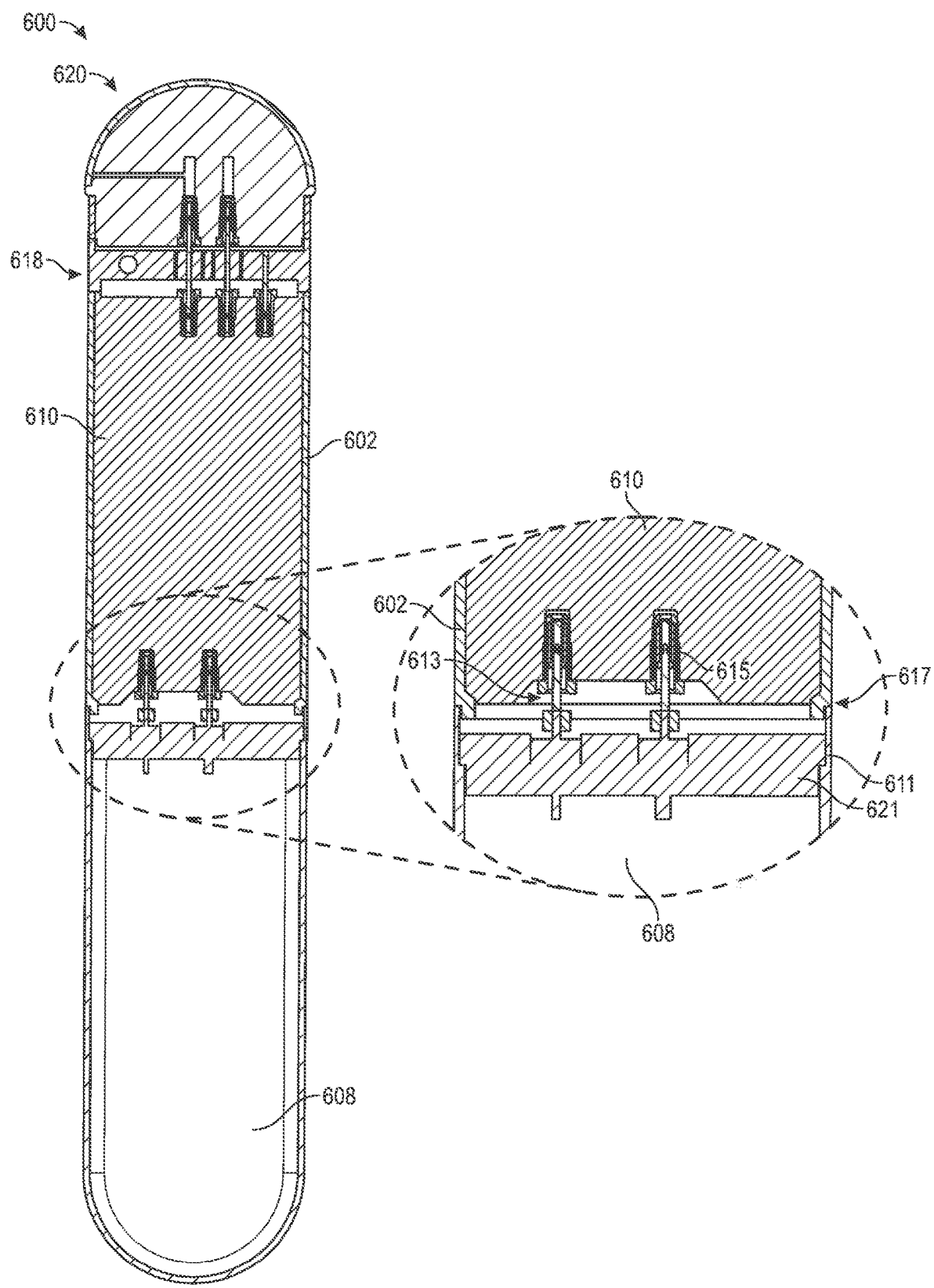
FIG. 6B illustrates the IMD in an assembled position with the battery 608 attached to the device housing in accordance with embodiments herein.

FIG. 6B illustrates the IMD 600 in an assembled position with the battery 608 attached to the device housing 602. Detail A is provided to show the interface in more detail between the battery 608 and the device housing 602. The battery 608 includes a battery feedthrough 621 that forms a hermetic seal with the battery shell 611 to isolate an interior of the battery 608 from the external environment. The battery terminals 613 extend from the battery feedthrough 621 and are received within and electrically coupled to the battery receptacles 615 that are provided on the hybrid circuit for the electronics module 610. When the device housing 602 is mounted to the battery 608, a battery-to-case interface 617 there between is sealed around the perimeter of the IMD 100, such as through welding or in other bonding technique.

In the embodiments described herein, the electrode retention region is provided along a side of the header, while the antenna retention platform extends from a distal end of the header. Optionally, the locations of the electrode retention region and antenna retention platform, and the corresponding electrode and antenna, may vary. By way of example, the antenna retention platform may extend from one side of the header, while the electrode retention region is provided on the opposite side of the header. As another example, the electrode retention region (and electrode) may be provided along the distal end of the header, while the antenna retention platform (and antenna) extends along one or both sides of the header. As yet another example, the electrode retention region may be formed to extend along at least a portion of the distal end of the header as well as wrapping around one side (or both sides) of the header (e.g., in a full or partial dome a shape). When the electrode retention region is provided at the distal end of the header, the antenna retention platform (and the antenna) may be provided along one or both sides, as well as extending about one or both ends of the header.

Next, an alternative embodiment is described in connection with FIGS. 7A-7B.

Figure 7A:
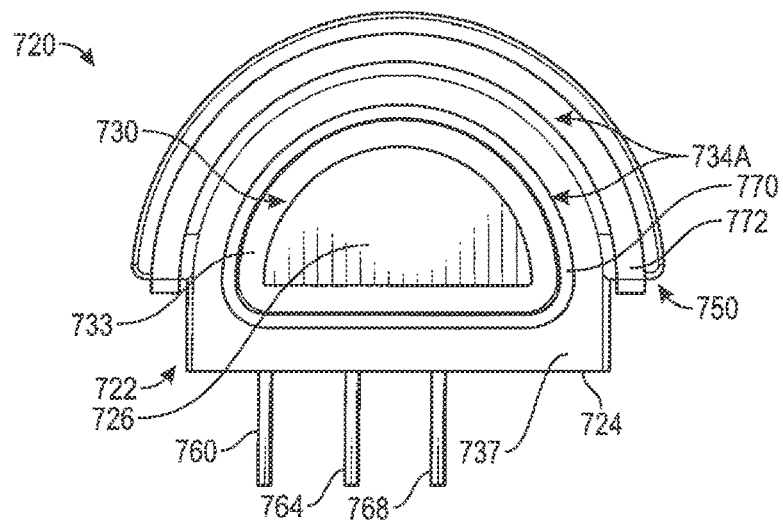
FIG. 7A illustrates a side perspective view of a header formed in accordance with embodiments herein.
Figure 7B:
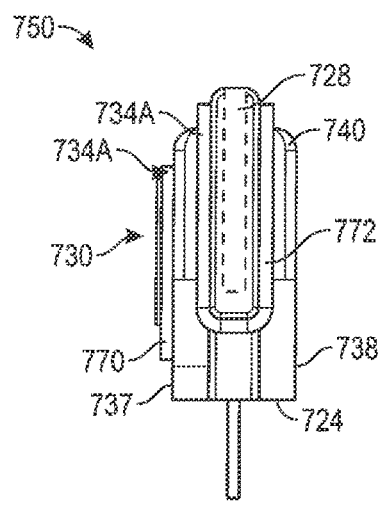
FIG. 7B illustrates an end perspective view of a header formed in accordance with embodiments herein.

FIGS. 7A and 7B illustrate side and end perspective views, respectively, of a header 720 formed in accordance with embodiments herein. The header 720 generally includes a common shape as in FIGS. 2A and 2B. The main body 722 represents a solid (non-hollow) body formed of a generally homogeneous ceramic material that includes one or more plated traces formed therein. The main body 722 includes a proximal mounting end 724, sidewalk 737, 738 and a curved distal end 740. The solid body of the ceramic material forming the main body 722 has exterior surfaces formed with projecting and recessed features to define an electrode retention region 730 and an antenna retention platform 750. Details of the electrode retention region 730 and antenna retention platform 750 are discussed below in more detail in connection with FIGS. 8A and 8B.

An antenna (as denoted by dashed line 728 in FIG. 7B) is integral and embedded within the antenna retention platform 750 and extends along an interior cavity within the antenna retention platform 750 proximate to the distal end 740. An electrode 726 is provided on the sidewall 737 within the electrode retention region 730. The electrode retention region 730 is surrounded by a rib 733, while the electrode 726 fits within the rib 733. The mounting end 724 has antenna, electrode and ground pins 760, 764, 768 projecting therefrom and configured to be electrically coupled to the electronics module within the device housing 702 of the IMD 700 in a feedthrough-less configuration. In the example of FIGS. 7A and 7B, the feedthrough assembly has been removed entirely and the pins 760, 764, 768 are inserted directly into receptacles mounted within a proximal end of the device housing.

The header 720 includes a shell that differs from the shell 734 of FIGS. 2A-5B. In the embodiment of FIGS. 7A-11, the shell comprises a multipart ring frame 734A mounted on the main body 722 (FIGS. 7A and 7B) and a header shell segment 734B that is formed with the device housing 702 (FIGS. 9, 7A and 7B). The ring frame 734A includes an electrode frame 770 and an antenna frame 772. The ring frame 734A is joined to the main body 722 along the interfaces there between to form a hermetic seal.

Figure 7C:
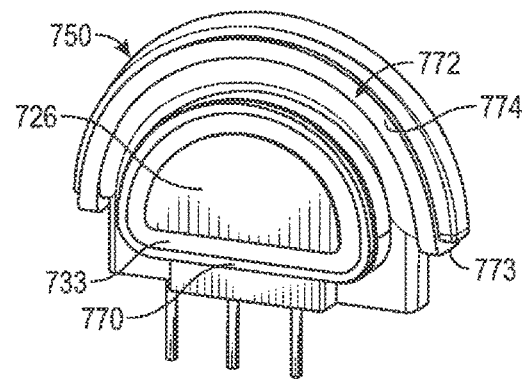
FIG. 7C illustrates a front perspective view of the header of FIGS. 7A and 7B in accordance with embodiments herein.

FIG. 7C illustrates a front perspective view of the header 720 of FIGS. 7A and 7B. As shown in FIG. 7C, the electrode frame 770 extends about the rib 733 and is electrically isolated from the electrode 726. In the present example, the electrode frame 770 generally includes a D shape, substantially similar to the D shape of the rib 733. The antenna frame 772 includes side rails 774 that are bent in a C-shape to follow along both sides of the antenna retention platform 750. The antenna frame 772 includes end linking portions 773 that wraps over opposite ends of the antenna retention platform 750 such that the antenna frame 772 substantially surrounds and follows a contour of the antenna retention platform 750.

Figure 8A:
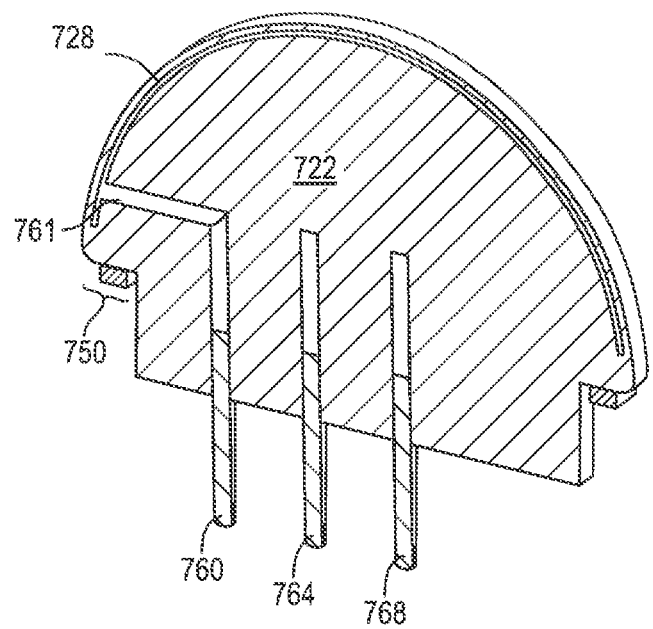
FIG. 8A illustrates a side sectional view through the main body of the header of FIG. 7A in accordance with embodiments herein.
Figure 8B:
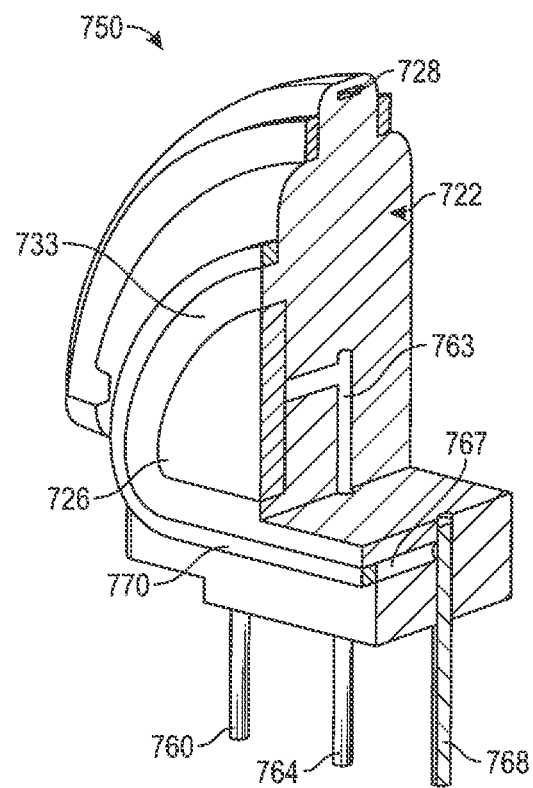
FIG. 8B illustrates an end sectional view through the main body of the header of FIG. 7A in accordance with embodiments herein.
Figure 9:
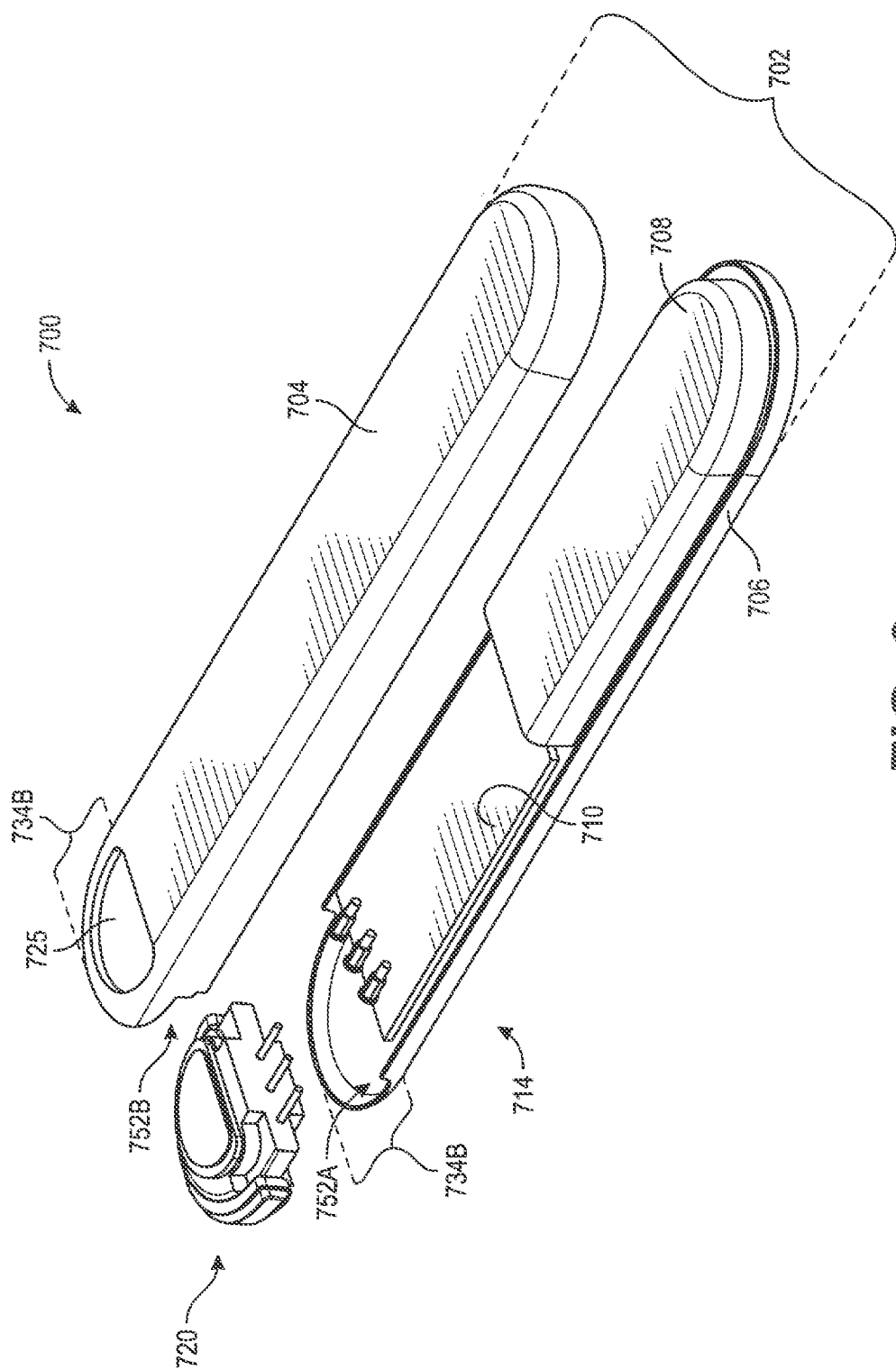
FIG. 9 illustrates an exploded perspective view of an IMD that includes the header of FIGS. 7A-8B in accordance with embodiments herein.

FIGS. 8A and 8B illustrate side and end sectional views, respectively, through the main body of the header of FIG. 7A. The antenna, electrode and ground pins 760, 764 and 768 are inserted into conductive traces formed within the ceramic material of the main body 722 of the header. As shown in FIG. 8A, the antenna pin 760 is joined with a conductive trace 761 that is coupled to an end of the antenna 728. The antenna 728 is embedded within the antenna retention platform 750. As shown in FIG. 8B, the electrode pin 764 is joined to a conductive trace 763 that is electrically coupled to the electrode 726. The ground pin 768 is joined with a conductive trace 767 that is electrically coupled to the electrode frame 770. The ground pin 768 defines a ground source once the electrode frame 770 is welded or otherwise bonded to the device housing. The end sectional view in FIG. 8B also illustrates the stepped arrangement in which the electrode frame 770 fits upon the rib 733 in the header main body 722, as well as the manner in which the antenna frame 772 extends along opposite sides of the antenna retention platform 750.

FIG. 9 illustrates an exploded perspective view of an IMD 700 that includes the header 720 of FIGS. 7A-8B in accordance with embodiments herein. The device housing 702 is formed with top and bottom case portions 704, 706 joined with one another to enclose a battery 708 and electronics module 710 (provided on a hybrid circuit). The electronics module 710 includes a set of receptacles 712 provided proximate to a proximal end 714 of the device housing 702. The receptacles 712 are configured to receive and electrically couple with pins 760, 764, 768 extending from a bottom side of the header 720 to provide a feedthrough-less configuration for interconnecting the header 720 and the electronics module 710.

The top and bottom case portions 704, 706 also include header shell segments 734B formed in a monolithic manner with a remainder of the top and bottom case portions 704, 706. The header shell segment 734B in the top case 704 includes an opening 725 that is shaped and dimensioned to receive and expose the electrode 726. An interior dimension of the opening 725 substantially corresponds to an exterior dimension of the electrode frame 770, such that when joined, the electrode frame 770 and top case 704 are bonded (e.g., welded) to one another about the opening 725. The header shell segments 734B mate with one another to overlap the sides of the main body 722 of the header 720 and to substantially enclose the header 720 there between. The header shell segments 734B include corresponding notched out portions 752A and 752B that combine to form an opening, through which the antenna retention platform 750 projects.

By way of example, during the assembly process, the battery 708 is attached to the electronics module 710 through the corresponding interface. The battery 708 and electronics module 710 are installed into the bottom case 706. Thereafter, the header 720 is attached to the electronics module 710 by inserting the pins 760, 764, 768 into the receptacles 712. The header 720, electronics module 710 and battery 708 are placed on the bottom case 706 with the antenna retention platform 750 extending from the notched up portion 752A Next, the top case 704 is mounted to the bottom case 706 to enclose the header 720, battery 708 and electronics module 710, while the electrode 726 is exposed to the opening 725. Thereafter, the interfaces between the top and bottom case 704, 706 are sealed, such as through a welding process or other bonding technique to hermetically seal the interior components of the IMD 700.

Figure 10A:
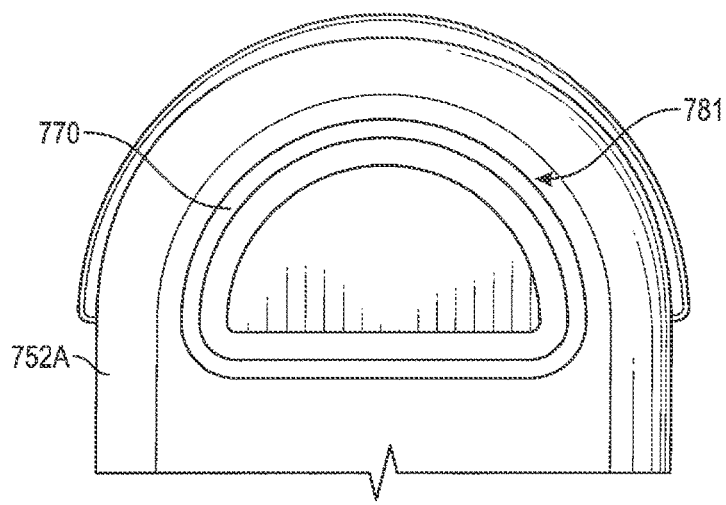
FIG. 10A illustrates a side view of the proximal end of the IMD when fully assembled in accordance with embodiments herein.
Figure 10B:
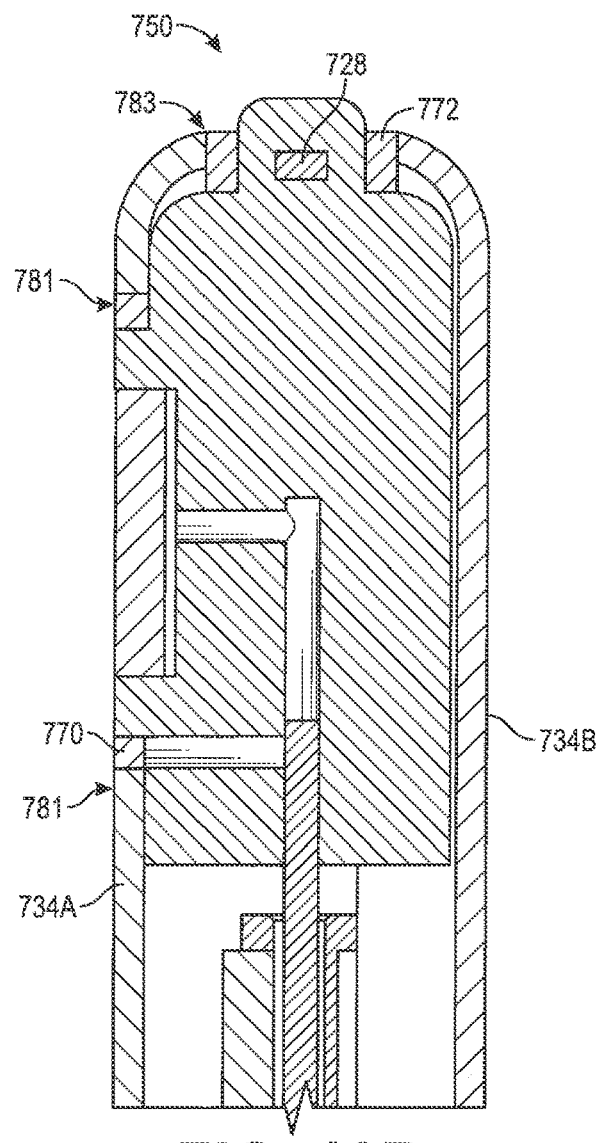
FIG. 10B illustrates an end sectional view of the proximal end of the IMD when fully assembled in accordance with embodiments herein.

FIGS. 10A and 10B illustrate a side view and an end sectional view of the proximal end of the IMD 700 when fully assembled. An interface 783 between the header shell segments 752A, 752B is welded or otherwise bonded to the antenna frame 772, and an interface 781 between the opening 725 and the electrode frame 770 is welded or otherwise bonded to hermetically seal the header 720 within the device housing 702. The antenna 728 is embedded within the antenna retention platform 750 in an integrated manner to surround the antenna with dielectric borders that separate the antenna 728 from adjacent portions of the header shell segments 734B by a predetermined spacing to limit or entirely prevent antenna coupling between the antenna 728 and the adjacent portions of the header shell segments 734B. The platform 750 is formed of ceramic which has a relatively high dielectric constant, as compared to other materials surrounding conventional antenna designs. Accordingly, embodiments herein enable the borders to have a relatively thin thickness, thereby allowing a relatively small spacing between the antenna 728 and the proximal portions of the header shell segments 734B, as compared to conventional antenna designs. As explained herein, it is desirable to avoid antenna coupling between the antenna 728 and the header shell segments 734B as antenna coupling introduces additional capacitance into the transmission characteristics of the antenna 728, which would in turn require the antenna to include additional features to offset the added antenna coupling capacitance (e.g., adding a wide plated section and/or a zigzag pattern). By avoiding antenna coupling, embodiments herein avoid the need for additional offsetting antenna features. By way of example, the antenna 728 may be formed as a monopole open loop antenna that has a singular arced curvature that bends along a relatively constant arc within a single plane.

Figure 11:
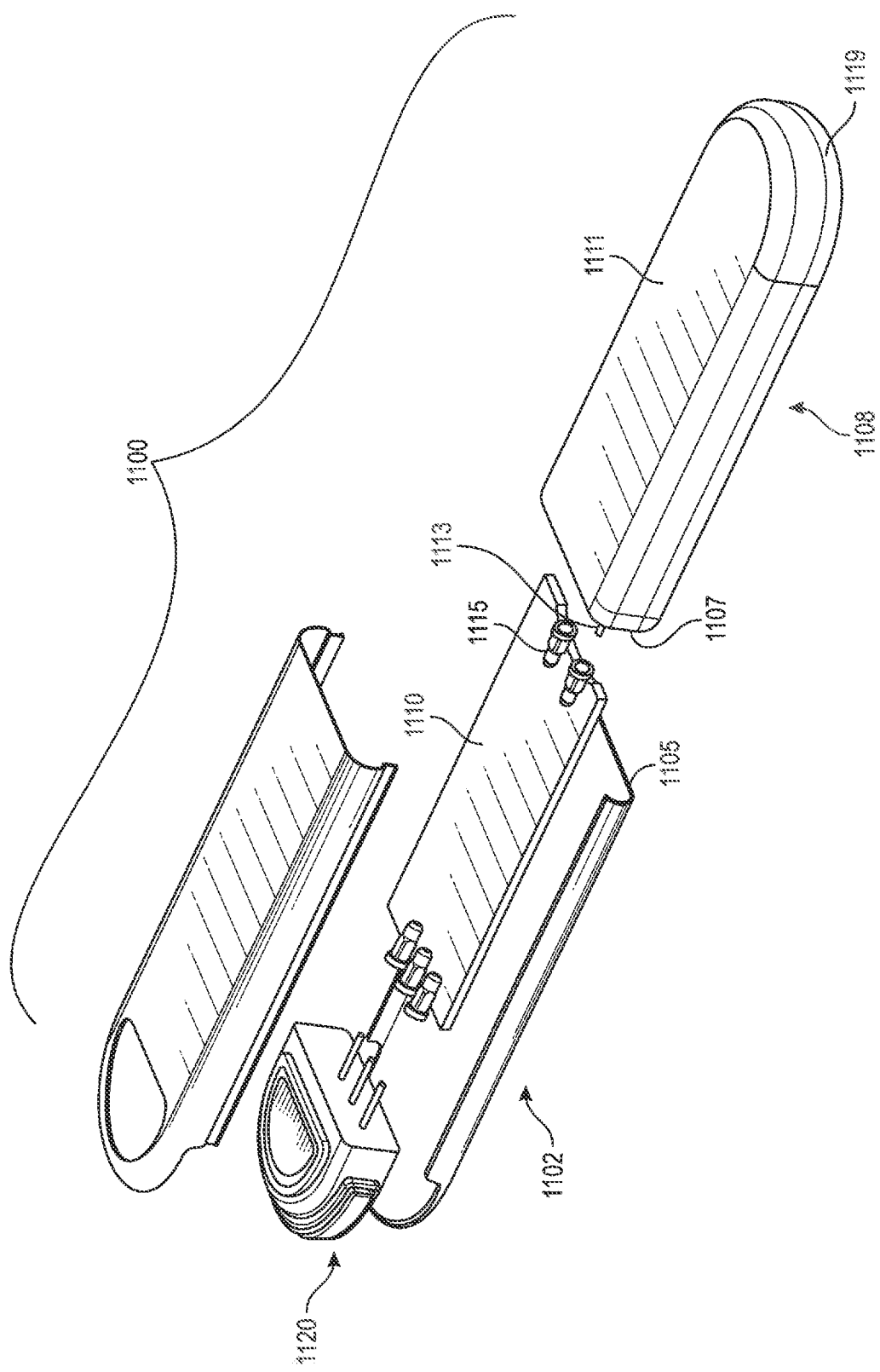
FIG. 11 illustrates an IMD formed in accordance with an alternative embodiment.

FIG. 11 illustrates an IMD 1100 formed in accordance with an alternative embodiment. The IMD 1100 includes a header 1120 and electronics module 1110 that are formed generally in the same manner as described above in connection with FIGS. 7A-10B. The embodiment of FIG. 11 differs from the embodiment of FIGS. 7A-10B in that a battery 1108 is provided separate from the device housing 1102. In FIG. 11, a separate standalone battery 1108 is provided that has a battery shell 1111 formed of a material intended to be exposed to and biocompatible with the physiologic environment of the implant area. The battery 1108 is not enclosed within the device housing 1102. The battery 1108 is provided with battery terminals 1113 extending therefrom. A second electrode 1119 is provided on the distal end of the battery 1108.

The header 1120 is connected to the electronics module 1110 in a feedthrough-less configuration, and the electronics module 1110 and the header 1120 are enclosed within the device housing 1102. A distal end 1105 of the device housing 1102 is abutted against and engages a proximal end 1107 on the battery shell 1111. The battery terminals 1113 electrically engage battery receptacles 1115 that are provided with the electronics module 1110. The electrical connections between the header 1120, electronics module 1110 and battery 1108 are generally similar to the electrical connections described and illustrated in connection with FIG. 6B.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An implantable medical device, comprising:
   a device housing having electronics module therein;
   an electrode;
   an antenna;
   a header having a main body,
   the main body formed of a ceramic material that includes side walls, a distal end and a proximal mounting end, the main body having an electrode retention region and an antenna retention platform, the antenna extending along the antenna retention platform, the electrode provided at the electrode retention region, the mounting end including electrode and antenna connectors, the main body includes a first plated trace formed through the ceramic material to be electrically coupled to the electronics module in the device housing between the antenna and the antenna connector, the main body including a second plated trace formed through the ceramic material between the electrode and the electrode connector; and
   a shell mounted over the main body, the shell having openings there through to expose the electrode and the antenna through the one of the side walls and the distal end, respectively, of the main body, the shell bonded to the device housing, wherein the shell and the device housing are formed of a common conductive material, and wherein the electrode retention recess and antenna retention platform electrically separate the electrode and antenna from the shell and device housing.

2. The device of claim 1, wherein the main body represents a solid body formed of a generally monolithic homogeneous ceramic material that includes the first and second plated traces formed therein, the solid body of the ceramic material having an exterior surface formed with projecting and recessed features to define the electrode retention region and the antenna retention platform.

3. The device of claim 1, further comprising a feed-through assembly joined between the device housing and the header, the feed-through assembly including conductors having distal ends connected to the electronics module and having proximal ends projecting from the feed-through assembly and joined to the antenna connector and electrode connector to electrically couple the electrode and antenna to the electronics module in the device housing.

4. The device of claim 1, wherein the antenna is embedded within the antenna retention platform and extends along an interior cavity within the platform proximate to the distal end.

5. An implantable medical device, comprising:
   a device housing having an electronics module therein;
   an electrode;
   an antenna;
   a header having a main body, the main body formed of a ceramic material that includes side walls, a distal end and a proximal mounting end, the main body having an electrode retention region and an antenna retention platform, the antenna extending along the antenna retention platform, the electrode provided at the electrode retention region, the mounting end including electrode and antenna connectors, the main body includes a first plated trace formed through the ceramic material to be electrically coupled to the electronics module in the device housing between the antenna and the antenna connector, the main body including a second plated trace formed through the ceramic material between the electrode and the electrode connector, wherein the header is directly mounted to a proximal end of the device housing in a feedthrough-less configuration.

6. The device of claim 5, further comprising a shell mounted over the main body, the shell having openings there through to expose the electrode and the antenna through the one of the side walls and the distal end, respectively, of the main body, the shell bonded to the device housing.

7. The device of claim 6, wherein the shell includes first and second shell case portions that include notched out portions that combine to form an opening through which the antenna retention platform projects.

8. The device of claim 6, wherein the device housing includes elongated opposed first and second cases that include header shell segments, the header shell segments mating with one another to overlap the side walls of the main body of the header, with at least one of the header shell segments having an opening there through to expose the electrode from the corresponding side of the header.

9. The device of claim 6, wherein the shell and the device housing are formed of a common conductive material, and wherein the electrode retention recess and antenna retention platform electrically separate the electrode and antenna from the shell and device housing.

10. An implantable medical device, comprising:
    a device housing having an electronics module therein;
    an electrode;
    an antenna;
    a header having a main body, the main body formed of a ceramic material that includes side walls, a distal end and a proximal mounting end, the main body having an electrode retention region and an antenna retention platform, the antenna extending along the antenna retention platform, the electrode provided at the electrode retention region, the mounting end including electrode and antenna connectors, the main body includes a first plated trace formed through the ceramic material to be electrically coupled to the electronics module in the device housing between the antenna and the antenna connector, the main body including a second plated trace formed through the ceramic material between the electrode and the electrode connector; and
    a shell mounted over the main body, the shell having openings there through to expose the electrode and the antenna through the one of the side walls and the distal end, respectively, of the main body, the shell bonded to the device housing, wherein the shell comprises a multipart ring frame mounted on the main body and a header shell segment formed with the device housing.

11. The device of claim 10, wherein the ring frame includes an electrode frame surrounding the electrode retention region and an antenna frame surrounding the antenna retention platform, the electrode and antenna frames bonded to the header shell segment.

12. The device of claim 10, wherein the device housing includes first and second case portions that include first and second header shell segments, respectively, the ring frame mating with and bonded to the first and second header shell segments.

13. An implantable medical device, comprising:
    a device housing having an electronics module therein;
    an electrode;

an antenna; and a header having a main body, the main body formed of a ceramic material that includes side walls, a distal end and a proximal mounting end, the main body having an electrode retention region and an antenna retention platform, the antenna extending along the antenna retention platform, the electrode provided at the electrode retention region, the mounting end including electrode and antenna connectors, the main body includes a first plated trace formed through the ceramic material to be electrically coupled to the electronics module in the device housing between the antenna and the antenna connector, the main body including a second plated trace formed through the ceramic material between the electrode and the electrode connector a battery having a battery shell formed of a material to be exposed to and biocompatible with a physiologic environment of the implant area, the battery connected to the electronics module and not enclosed within the device housing.

14. A header for an implantable medical device, comprising:

an electrode;

an antenna;

a main body formed of a ceramic material that includes side walls, a distal end and a proximal mounting end, the main body having an electrode retention region and an antenna retention platform, the antenna extending along the antenna retention platform, the electrode provided at the electrode retention region, the mounting end including electrode and antenna connectors, to be electrically coupled to an electronics module in a device housing, wherein the main body includes a first plated trace formed through the ceramic material between the antenna and the antenna connector, the main body including a second plated trace formed through the ceramic material between the electrode and the electrode connector; and a shell mounted over the main body, the shell having openings there through to expose the electrode and the antenna through the one of the side walls and the distal end, respectively, of the main body, the shell bonded to the device housing, wherein the shell and the device housing are formed of a common conductive material, and wherein the electrode retention recess and antenna retention platform electrically separate the electrode and antenna from the shell and device housing.

15. The header of claim 14, wherein the main body represents a solid body formed of a generally homogeneous ceramic material that includes the first and second plated traces formed therein, the solid body of the ceramic material having an exterior surface formed with projecting and recessed features to define an electrode retention region and an antenna retention platform.

16. A method to provide an implantable medical device, comprising:

mounting an electronics module in a device housing;

providing a header by:

forming a main body of a ceramic material that includes side walls, a distal end and a proximal mounting end, the main body having an electrode retention region and an antenna retention platform;

locating an antenna to extend along the antenna retention platform;

locating an electrode at the electrode retention region;

inserting electrode and antenna connectors at the mounting end;

wherein the main body includes a first plated trace formed through the ceramic material between the antenna and the antenna connector; and wherein the main body includes a second plated trace formed through the ceramic material between the electrode and the electrode connector; and attaching the header to the device housing with the antenna and electrode connectors electrically coupled to the electronics module in the device housing, wherein attaching operation includes directly mounting the header to a proximal end of the electronics module in a feedthrough-less configuration.

17. The method of claim 16, wherein the forming operation includes:

forming the main body as a solid body of a generally monolithic homogeneous ceramic material that includes the first and second plated traces formed therein; and forming an exterior surface of the solid body with projecting and recessed features to define the electrode retention region and the antenna retention platform.

18. The method of claim 16, further comprising:

mounting a shell over the main body;

providing openings through the shell to expose the electrode and the antenna through the one of the side walls and the distal end, respectively, of the main body; and bonding the shell to the device housing.

19. The method of claim 16, further comprising enclosing the header and electronics module in the device housing.

* * * * *